(12) United States Patent
Tsukernik et al.

(10) Patent No.: US 6,798,198 B2
(45) Date of Patent: Sep. 28, 2004

(54) FLUID SUPPORTS FOR SENSORS

(75) Inventors: Vladimir Tsukernik, West Roxbury, MA (US); Neil J. Goldfine, Newton, MA (US); Andrew P. Washabaugh, Chula Vista, CA (US); Darrell E. Schlicker, Watertown, MA (US); Karen E. Walrath, Arlington, MA (US); Eric Hill, Watertown, MA (US); Vladimir A. Zilberstein, Chestnut Hill, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 0 days.

(21) Appl. No.: 10/348,339

(22) Filed: Jan. 21, 2003

(65) Prior Publication Data

US 2003/0155914 A1 Aug. 21, 2003

Related U.S. Application Data

(63) Continuation of application No. 10/172,834, filed on Jun. 13, 2002, now abandoned, which is a continuation-in-part of application No. 10/102,606, filed on Mar. 19, 2002, now abandoned, which is a continuation of application No. 09/946,146, filed on Sep. 4, 2001, now abandoned.
(60) Provisional application No. 60/297,841, filed on Jun. 13, 2001, and provisional application No. 60/231,776, filed on Sep. 12, 2000.

(51) Int. Cl.[7] ................ G01N 27/82; G01R 33/12

(52) U.S. Cl. ............... 324/262; 324/261; 324/238; 324/220; 324/242; 324/219

(58) Field of Search .................. 324/261, 262, 324/219, 220, 221, 237, 238, 240, 242, 243

(56) References Cited

U.S. PATENT DOCUMENTS

| | | | | |
|---|---|---|---|---|
| 2,622,125 A | * | 12/1952 | Bender | 324/220 |
| 4,303,884 A | * | 12/1981 | Malick | 324/220 |
| 5,023,549 A | * | 6/1991 | Dau et al. | 324/220 |
| 5,047,719 A | | 9/1991 | Johnson et al. | |
| 5,278,498 A | | 1/1994 | Vernon et al. | |
| 5,315,234 A | | 5/1994 | Sutton, Jr. et al. | |
| 5,442,286 A | * | 8/1995 | Sutton et al. | 324/242 |
| 5,453,689 A | | 9/1995 | Goldfine et al. | |
| 6,545,469 B1 | | 4/2003 | Batzinger et al. | |

* cited by examiner

Primary Examiner—Jay Patidar
(74) Attorney, Agent, or Firm—Hamilton, Brook, Smith & Reynolds, P.C.

(57) ABSTRACT

Pressurized elastic support structures or balloons are used to press flexible sensors against the surface a material under test. Rigid support elements can also be incorporated into the inspection devices to maintain the basic shape of the inspection structure and to facilitate positioning of the sensors near the test material surface. The rigid supports can have the approximate shape of the test material surface or the pressurization of one or more balloons can be used to conform the sensor to the shape of the test material surface.

31 Claims, 16 Drawing Sheets

FLUID SUPPORTS FOR SENSORS

RELATED APPLICATIONS

This application is a continuation of U.S. application Ser. No. 10/172,834, filed Jun. 13, 2002, now abandoned, which claims the benefit of U.S. Provisional Application No. 60/297,841, filed Jun. 13, 2001, and is a continuation-in-part of U.S. application Ser. No. 10/102,606, filed Mar. 19, 2002, now abandoned, which is a continuation of U.S. application Ser. No. 09/946,146, filed Sep. 4, 2001, now abandoned, which claims the benefit of U.S. Provisional Application No. 60/231,776, filed on Sep. 12, 2000.

The entire teachings of the above applications are incorporated herein by reference.

BACKGROUND

The nondestructive evaluation of materials for damage and defects often involves the inspection of curved surfaces having limited access, such as engine disk slots, helicopter propulsion components, turbine blades, bolt holes, and automotive components. Typically, the defect appears when the inspection sensor, such as an eddy current sensor, is brought into intimate contact with the surface. For coverage over wide areas of the surface, this inspection requires the use of sensors that are formed into the shape of the curved surface or are fabricated onto a flexible backing that can conform to the shape of the surface.

Compliant substrates, such as foam or ferrite loaded substrates, have been used to enhance the performance of eddy-current sensors and allow sensor arrays to conform to a surface through the compliance of the substrate. These non-rigid substrates offer the advantage of conforming to a wide range of complex shapes, but often require a rigid inner core to maintain the general shape and can result in local variations in pressure on the sensor and a lack of adherence of the array to the surface of the material under test.

The shape of devices and gaps between devices has been controlled by the use of fluids such as water, air and oil for devices such as automobile tires, balloons used in angioplasty to clear arteries in the heart, and in air bearings. Often the desire is to maintain a specific shape without significant compliance after the shape has been established.

SUMMARY

In general, the invention addresses the limitations of compressible solid substrates for inspection of confined material surfaces by introducing fluid substrates enclosed in relatively rigid pre-shaped membrane materials or combinations of fluid filled "balloons" with compliant solids, such as foam or elastomers.

In some embodiments a cylindrical shaped balloon is used to press a noncompressible solid shuttle with the approximate shape of the material under test surface (e.g., an engine disk slot) against the material under test surface. Sensors placed on the surface of the shuttle are then used to inspect the material for flaws and defects or to characterize the material properties, such as coating thickness, electrical conductivity, or magnetic permeability.

In other embodiments, a chambered elastic support member, such as a balloon, and means for pressurizing this chamber, are used to locating a sensor near and against the material surface under inspection. For the inspection of electrically conducting materials and magnetic materials, the sensor can be an inductive or eddy current sensor or an eddy current sensor array. In certain embodiments, additional supports can be placed between the sensor and the elastic support. These supports can be rigid or made of an elastic material so that the supports can conform to the shape of the test material surface when the chamber is pressurized. For positioning the elastic support members near the surface of the test material, one embodiment has at least one rigid support element. In other embodiments, a rigid support element forms a core which is then surrounded by a plurality of elastic support members that can conform to the surface of the test material. To enhance the conformability of the sensor against the test material surface, an additional compressible layer, such as a foam, is placed between the support members and the sensor.

In yet other embodiments the sensor is located near the test material surface using both a rigid support member and a chambered elastic support member that can be pressurized. In some embodiments, the rigid support approximates the shape of the test material surface. In another embodiment, an additional compressible layer is placed between the support members and the sensor. In one embodiment, the pressurizable elastic support member is placed behind the sensor to press the sensor against the test material surface. The rigid support can include a rigid body, an actuated portion that can move when the chambered elastic support is pressurized, and a spring for restoring the positions when the pressure is removed. The pressurizable support can be placed between the body and the actuated portion. In another embodiment, the actuated portion presses against an opposing surface of the test material. The actuated portion can have a roller that is in contact with the opposing test material surface and facilitates smooth motion along the surface. In some embodiments, the rigid support forms a core structure that is surrounded by numerous pressurizable supports. In other embodiments, several rigid supports are placed between a pressurizable chamber and a sensor. In yet other embodiments, an additional compressible pad is placed between the rigid supports and the sensor.

Other embodiments have the sensor located near the test material surface using a rigid support member that approximates the shape of the test material surface, a chambered elastic support member than can be pressurized, and a compressible support layer behind the sensor. In some cases the test material surface is substantially concave and is in a partially enclosed region of the component where the ends of the component are used to access the test material surface. In one embodiment, convex tabs are placed on the back of the rigid insert to prevent contact between the insert and the surfaces of the component opposing the test material surface. In certain embodiments, the test material surface is an engine disk slot. In other embodiments, the inspection involves the measurement of surface roughness or surface damage, including fretting.

In yet other embodiments, the sensor is located near the test material surface using a rigid support member that approximates the shape of the test material surface and a chambered elastic support member than can be pressurized. In some embodiments, a flexible ring of a substantially non-expandable material encircles the pressurizable support member, a rigid support and a spring. The ring holds the components in place while the spring helps deflate the pressurizable chamber when the pressure source is removed. The flexible rings and components can be a removable insert for ease of repair when components break. In another embodiment, a second pressurizable elastic member is used to apply the pressure to the first pressurizable elastic material.

In another embodiment, a chambered elastic support member that can be pressurized presses a sensor against the surface of a test material and a support is used to adjust the sensor position. In one embodiment, the support is a rigid pipe that encloses the elastic member except for an opening that is spanned by the sensor. Applying pressure to the elastic member causes it to expand against the sensor and presses the sensor against the test material surface. In another embodiment, the support is a pair of cables that are placed on the sides of the elastic member and held in place by a flexible film. Pressurization of the elastic member causes it to expand against both the surface of the component opposite the test material surface and the sensor. The support can be a rigid rod that allows an operator to translate the sensor over the surface of the test material. Furthermore, an additional rigid support can be placed between the sensor and the elastic member, and a flexible ring of a substantially non-expandable material encircles the pressurizable elastic member, the additional rigid support and the sensor to hold the components in place.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention

FIG. 6b is a cross-sectional view of the probe of FIG. 6a.

DETAILED DESCRIPTION OF THE INVENTION

A description of preferred embodiments of the invention follows.

Figure 1:
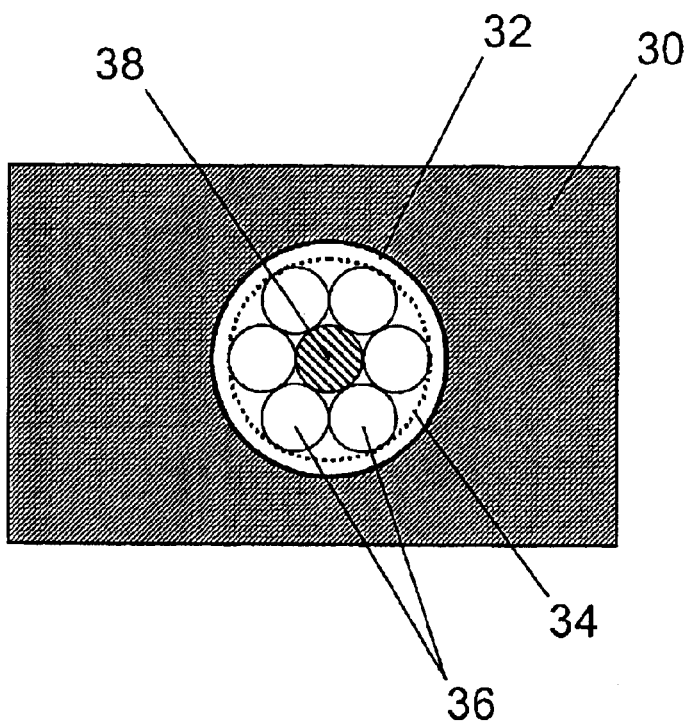
FIG. 1 is an illustration of a bolt hole probe with a fluid shuttle in accordance with the invention.

FIG. 1 shows a shuttle device for inspecting the inside of a circular opening 32 in a material under test (MUT) 30, such as a bolt hole. A flexible sensor or sensor array 34 is located between the central core 38 of the shuttle and the inner surface of the MUT. The core 38 can be an elastic material that can expand under pressure, such as a balloon that is inflated either pneumatically of hydraulically, so that the sensor 34 is near to or in contact with the MUT surface. In an embodiment, the flexible sensors or sensor arrays are eddy current sensors, described for example in U.S. Pat. No. 5,453,689 to Goldfine and Melcher, U.S. Pat. No. 5,047,719 to Johnson and Krampfner, and U.S. Provisional Application No. 60/276,997 filed Mar. 19, 2001, the entire teachings of which are incorporated herein by reference. In addition, a compliant solid (e.g., foam layer) may be included either between the solid shuttle and the array or between the array and the material under test.

In another embodiment, the core 38 of the shuttle is solid and surrounded by balloons 36. The sensor 34 is positioned between the balloons 36 and the MUT surface so that inflation of the balloons can move the sensor to be in contact with the test material. This use of multiple balloons can enhance the conformability of the sensor to the test surface as the pressure in individual balloons can be adjusted independently.

Figure 2:
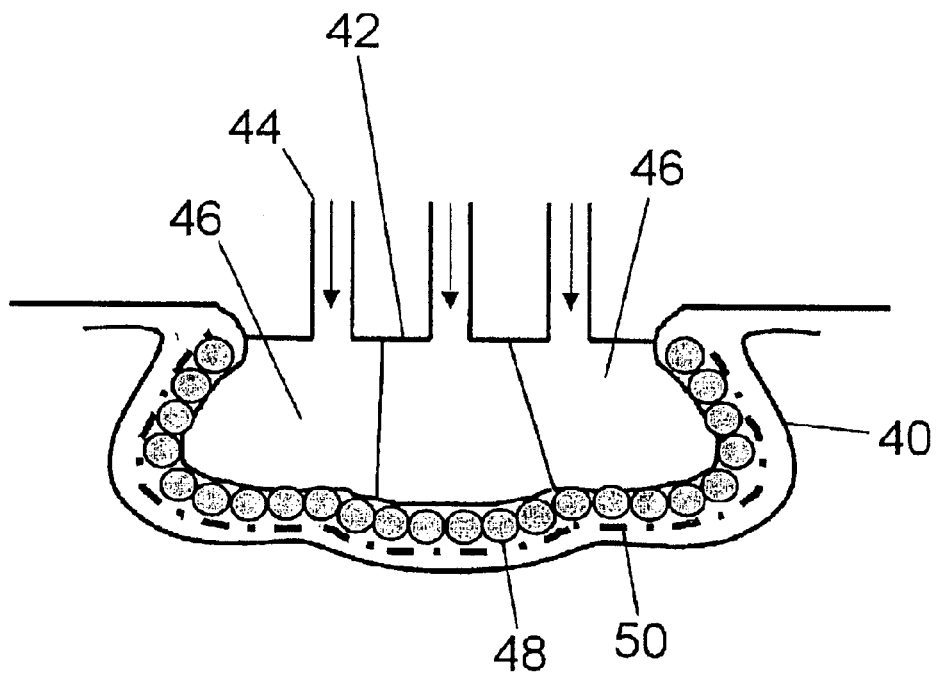
FIG. 2 is an illustration of a multiple fluid filled support chamber for a sensor array in accordance with the invention.

FIG. 2 shows a more complex design for a fluid filled support chamber. The sensor or sensor array 50 is positioned between the MUT surface 40 and one or more fluid filled support chambers or balloons 46. Fluid flow through conduits 44 in a back plate 42, preferably rigid, provides the pressure for inflating or deflating the chambers. Additional support or conformability can be provided by including rigid cylinder supports or support balloons 48 between the sensor 50 and the chambers 46. These balloons can be attached to each other and, in one embodiment, they can be enclosed in a larger balloon and attached to the inside of that balloon. In one embodiment, the composite balloon is extruded as an integrated part with chambers representing the balloons. These chambers may or may not be cylindrical and may be of varying shapes. By introducing fluids into individual balloons or groups of balloons at a controlled pressure the balloons will expand to form individual cylinders. These micro-cylinders combine to form a macro-shape that follows the contour of the material under test surface. The kinematics of filling balloons to form to a complex shape can be computed with computer models so that the required amount of fluid within each balloon can be predetermined to form a specific shape. Also, non-cylindrical balloons can be used as part of the composite, and an outside membrane may also be introduced to provide a smooth continuous surface for mounting the sensor array and pressing against the material under test. In another embodiment, hard solid strips or cylinders of substrate material are pressed against the array by a fluid filled inner cushion that conforms to the shape of the material under test. This reverses the roll of the hard shuttle with the foam outer layer. When cylinders are used a thread weave can be used to hold the composite together permitting the cylinder layer to conform to the shape of the slot while individual anchor cylinders are attached locally to the sensor array.

A variety of fluids can be used to expand the balloon element or chamber. These could include gases, such as air or nitrogen, or liquids, such as water, rheological fluids or ferrofluids. An advantage of electrorheological fluids and ferrofluids is that electrode elements can be added to the probe structure to impose electric or magnetic fields which, when passing through the electrorheological or ferro-fluids, causes a dramatic increase in the fluid viscosity and substantially cause the fluid to maintain it's shape. In this manner, the shape of the balloon structure can be "locked-in" after being expanded.

Figure 3:
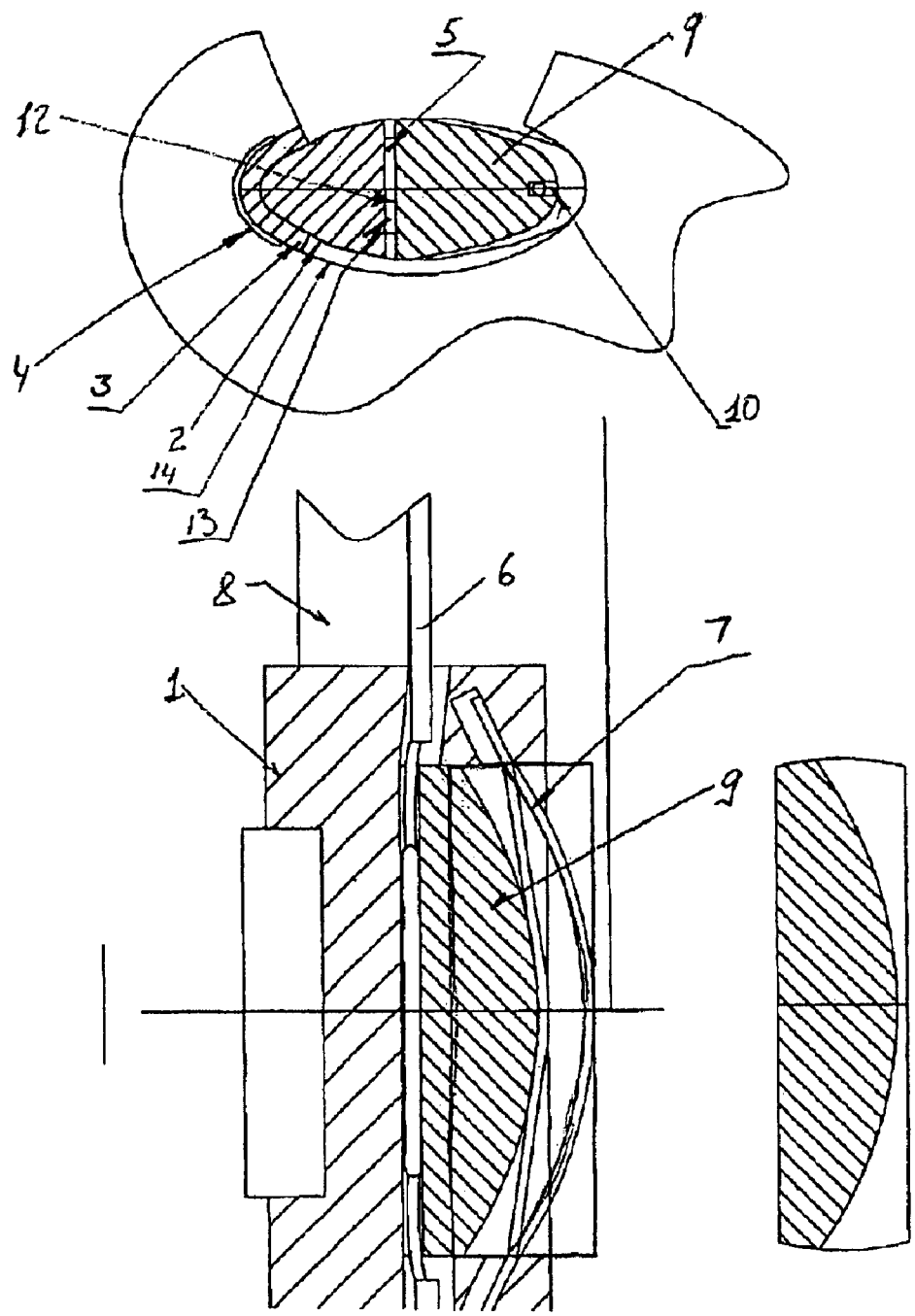
FIG. 3 is an illustration of a conformable probe with an expandable element located between two rigid elements.

An embodiment of an adjustable and conforming probe for curved surface inspections with flexible eddy current sensors is illustrated in FIG. 3. The probe includes a body 1, shoe 9, and expandable element 13 for compressing the sensor 4 against surface to be inspected. An additional layer of foam 3 helps to provide uniform pressure from the body section to the sensor. The parts are secured together by means of a straight spring wire spring 7. The balloon can be expanded in a controlled fashion so that the probe can be inserted into curved openings, such as disk slots, when the balloon is deflated, but intimate contact between the sensor and the test surface is maintained when the balloon is expanded.

The body 1 of FIG. 3 includes several components. The front body surface 2 is offset from the corresponding surface to be inspected 14 to provide ease of travel of the probe into the slot region. The flat flexible sensor 4 is located on the outside surface of the foam that faces an inner surface of the slot to be inspected. The foam layer thickness can be selected to maintain the desired compression of the sensor against the surface of the material under test (MUT), with thickness of 0.010 to 0.150 inches typical. Ideally the foam will provide enough compression for the sensor to substantially conform to the contour of the MUT. Thinner foam thicknesses can be used if the shape of the body section 2 is substantially the same as the contour of the MUT. The back body surface 5 is in contact with the balloon 13 and faces the corresponding surface 12 of the shoe 9. As shown in the cross-section in the lower portion of FIG. 3, the body 9 is shaped like a "C" to provide support around the shoe 9. Orifices for sleeve connections to the balloon 6, the groove for the spring 10 and the handle 8 are illustrated. The shoe is positioned inside the "C" shaped portion of the body 2, and its outer surface has the same general shape as the body. The shoe is held in position with the spring 7 in the groove 10. The spring compresses the shoe and body together, flattening the balloon when the balloon is deflated.

For inspections, the probe structure should be smaller than the slot in which the probe is to be inserted. The balloon can then be inflated, either pneumatically of hydraulically, which will move the shoe 9 out of the body 2 as it overcomes the spring 7 resistance. When the shoe reaches the back surface of the slot, the body (and sensor) will be compressed against the surface of the MUT. This inflation of the balloon can be maintained until a desired pressure is reached. This configuration has the advantage of ease of insertion into the slot, it can provide constant, controllable, and repeatable pressure on the sensor during measurements.

Figure 4:
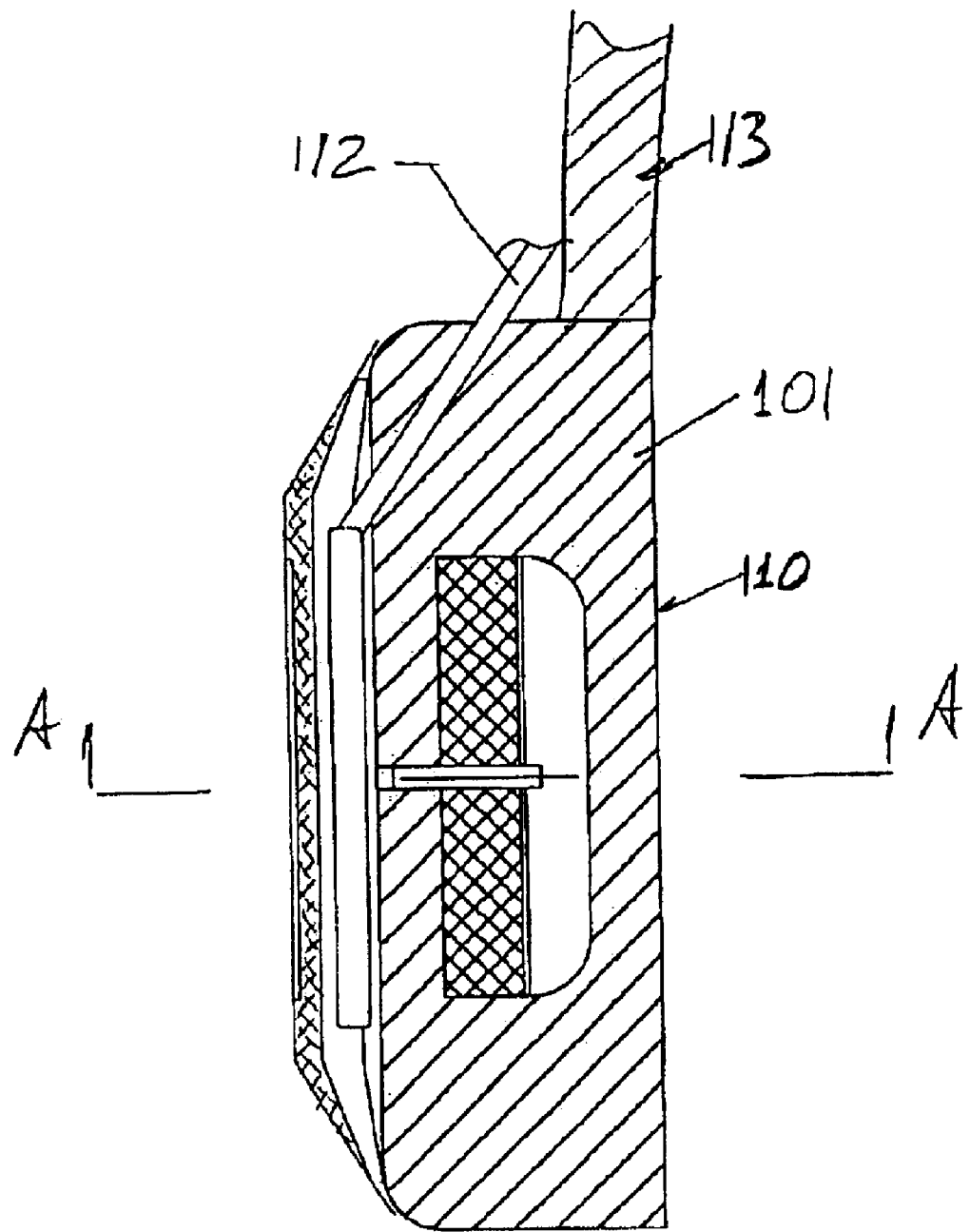
FIG. 4 is an illustration of a conformable probe with a balloon placed behind the sensing element.
Figure 5:
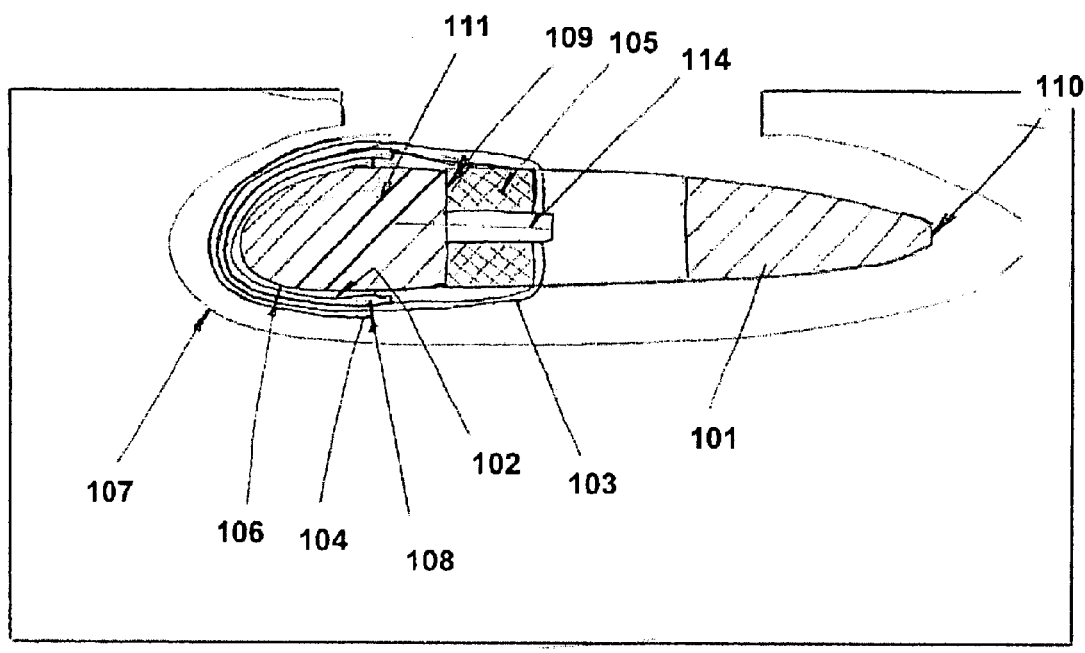
FIG. 5 is a cross-sectional view of the probe of FIG. 4.

The conformable probe configuration of FIG. 4 and FIG. 5 also uses a plastic balloon, except the balloon is placed between the probe body and the sensor. In this case the probe includes a body 101, the expandable element 102, a flexible but substantially non-expandable ring 103, and a foam spring 105 within the probe body. The flexible sensor 104 is attached to the outer surface of the ring 103 for inspection of the inner surface of the MUT. The front body surface 106 is roughly offset from the corresponding inner surface of the MUT to provide room for the sensor 104, balloon 102, and foam 108. The foam spring 105 located on the back body inner surface 109. The ring 103 surrounds the foam layer 108, balloon 102, strut 111 of the body and foam spring 105. The foam spring 105 stretches the ring 103 that compresses and flattens the balloon 102 against the surface 106. The body 109 has an "O"-shape that includes orifices for the balloon sleeves 112 and handle 113. The plastic pin 114 located on the surface 109 secures the position of the ring 103 and the foam spring 110, which also maintains the position of the sensor 104 as the balloon is inflated and deflated. The foam layer 108 may be unnecessary if the balloon itself can provide sufficient conformability with the test surface when inflated. An additional protective layer of a flexible but not expandable material, such as Kapton™, can also be placed on the outer surface of the sensor, between the sensor and the surface of the test material.

For inspections, the probe structure should be smaller than the opening, such as an engine disk slot, in which the probe is to be inserted. The balloon can then be inflated, either pneumatically of hydraulically, which will move left side of the ring together with the sensor to the surface of the MUT as it overcomes the resistance of the foam spring. When the sensor reaches the corresponding surface of the MUT, the body moves to the right until its right side touches the opposite side of the opening. After this inflation, the balloon maintains necessary pressure between the sensor and MUT. This configuration provides ease of insertion into the opening, can provide constant, controllable, and repeatable pressure on the sensor during measurements, and can accommodate a wide range of size of shape variations for surface for the MUT. Furthermore, the balloon serves to provide substantially even pressure against the entire backing of the sensor.

An alternative for the design shown in FIG. 5 is to use a roller on the back surface of the body 110. This would promote scanning of the shuttle over the surface of the MUT. In addition, a large static balloon 102 could be used to replace the foam support 108, body 111, foam spring 105 and pin 114. This balloon would be pressurized, prior to insertion into the slot containing the surface of the MUT, and would provide an essentially uniform pressure of the sensor against the MUT surface. The balloon would only have to be expanded at the beginning of testing, and would not require repeated inflation or deflation during repeated scans through the various slots. These configurations can all be used for either convex, concave open or closed MUT surfaces by changing the support structure configuration accordingly.

Figure 6A:
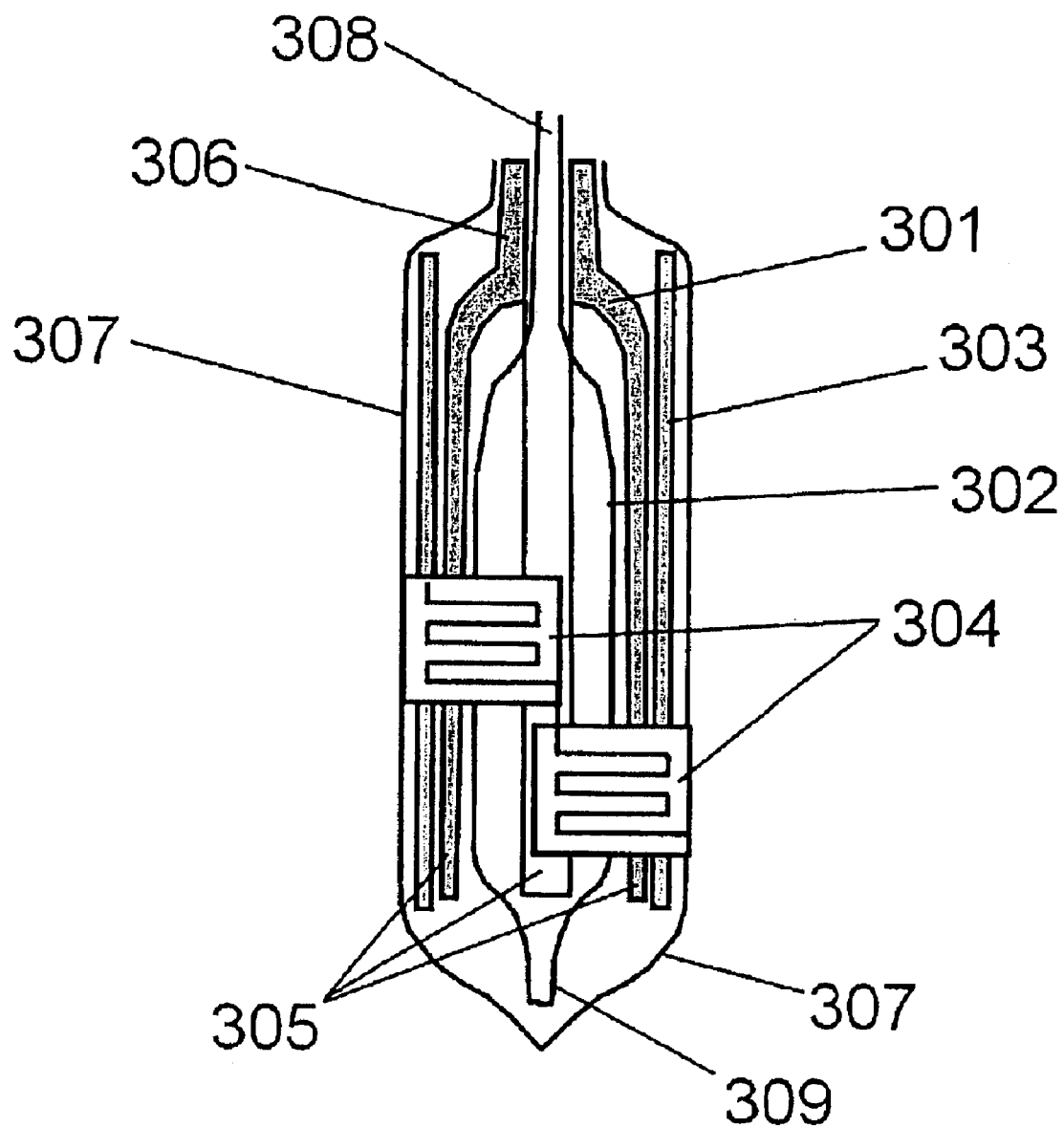
FIG. 6a is an illustration of a conformable probe suitable for the inspection of a hole.
Figure 6B:
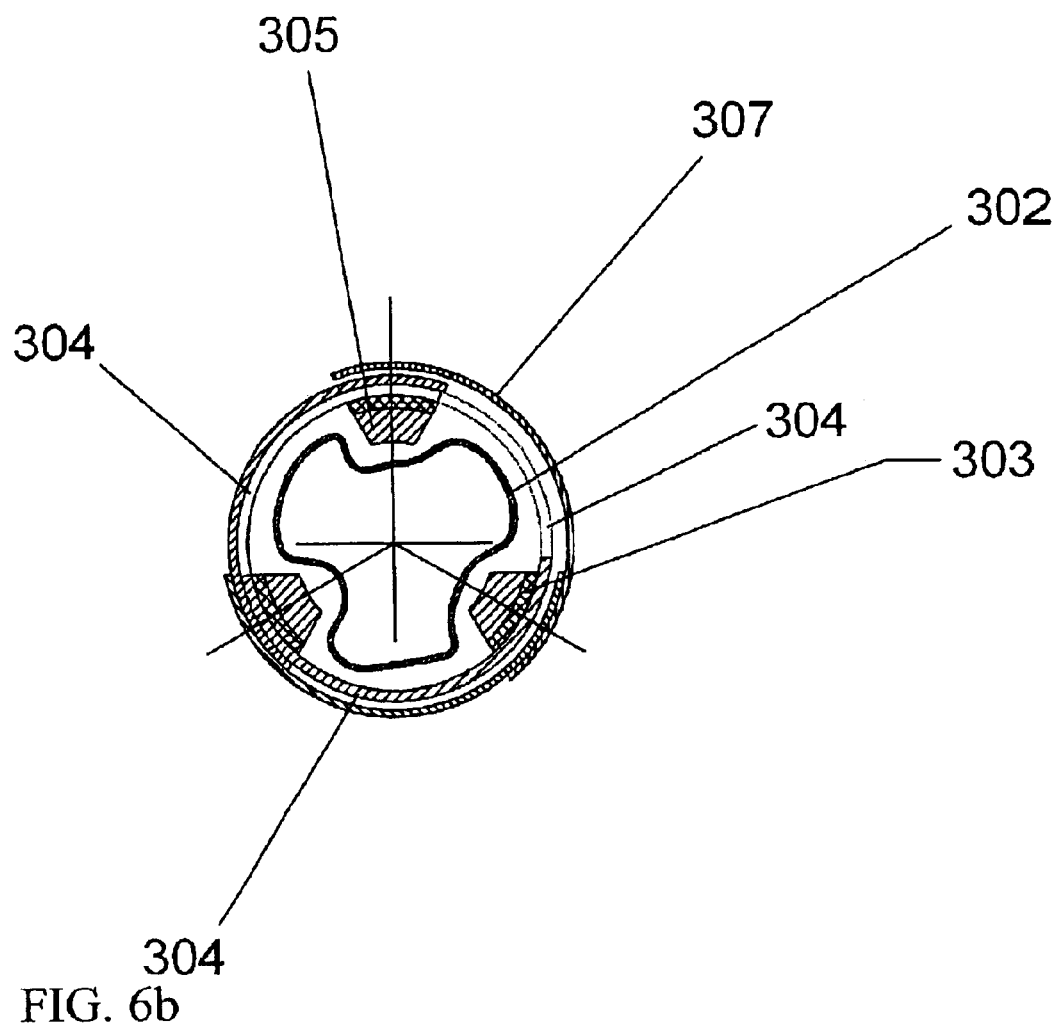

The conformable probe configuration of FIGS. 6a and 6b is suitable for the inspection of holes, both circular and non-circular or oval. The probe includes a body 301, foam pads 303, an expandable element like a plastic balloon 302, and at least two strips 307 (three are shown) of low coefficient of friction strong material, such as a Teflon™ or Kapton™ film. The sensor 304 (three segments are shown) is attached to the outer surface of the pads 303 for intimate contact with the surface of the MUT.

In this case, the body 301 is a collet including at least three prongs 305 of elastic solid plastic. The upper part of the body ends attaches to a handle 306. A balloon 302 is located inside the collet and coaxial to the collet. The distal sleeve of the balloon 309 is closed so that the balloon can be pressurized. The proximal sleeve of the balloon 308 passes through the handle 306 and is connected to the source of pressure (pneumatic or hydraulic).

The pads 303 are made of soft elastic plastic or foam. In one embodiment, the nominal thickness of these pads is between about 0.01 to 0.2 inches. They are located outside the collet on its circumference. The sensor 304 is divided into three segments. Each of them is bent so that they span a portion or a segment of the circumference and is attached to the corresponding pad at one point. Although designed for electromagnetic measurements, the elastic property of the sensor permits it to behave mechanically like a flat spring. The strips 307 are attached to the handle 306 on one side and bonded together on the another side.

In operation, this sensor shuttle is inserted into the hole by deflating the balloon so that the collet is collapsed. The outside diameter of the sensor and shuttle is designed to be smaller than the inside diameter of the hole, when the balloon is deflated, which eases insertion of the probe into the hole. After being positioned in the hole, the balloon is inflated. This opens the collet and stretches out the flexible elastic tube 303 in a radial direction that provides a radially directed pressure behind the sensor. The strips 307 then move apart along with the sensor rings. As the sensors, together with the tube 303 and strips 307, reach the inner hold surface, the increasing pressure inside the balloon compresses the sensor against the surface of the MUT with a metered (i.e., controlled) force. The entire inner surface of the hole could then be scanned by pulling the sensor shuttle along the axis of the hole since the sensor rings overlap the inspection area and provide for complete coverage. The prongs inside and strips outside secure the probe from destruction and provide constant sensor position during inspection.

Figure 7:
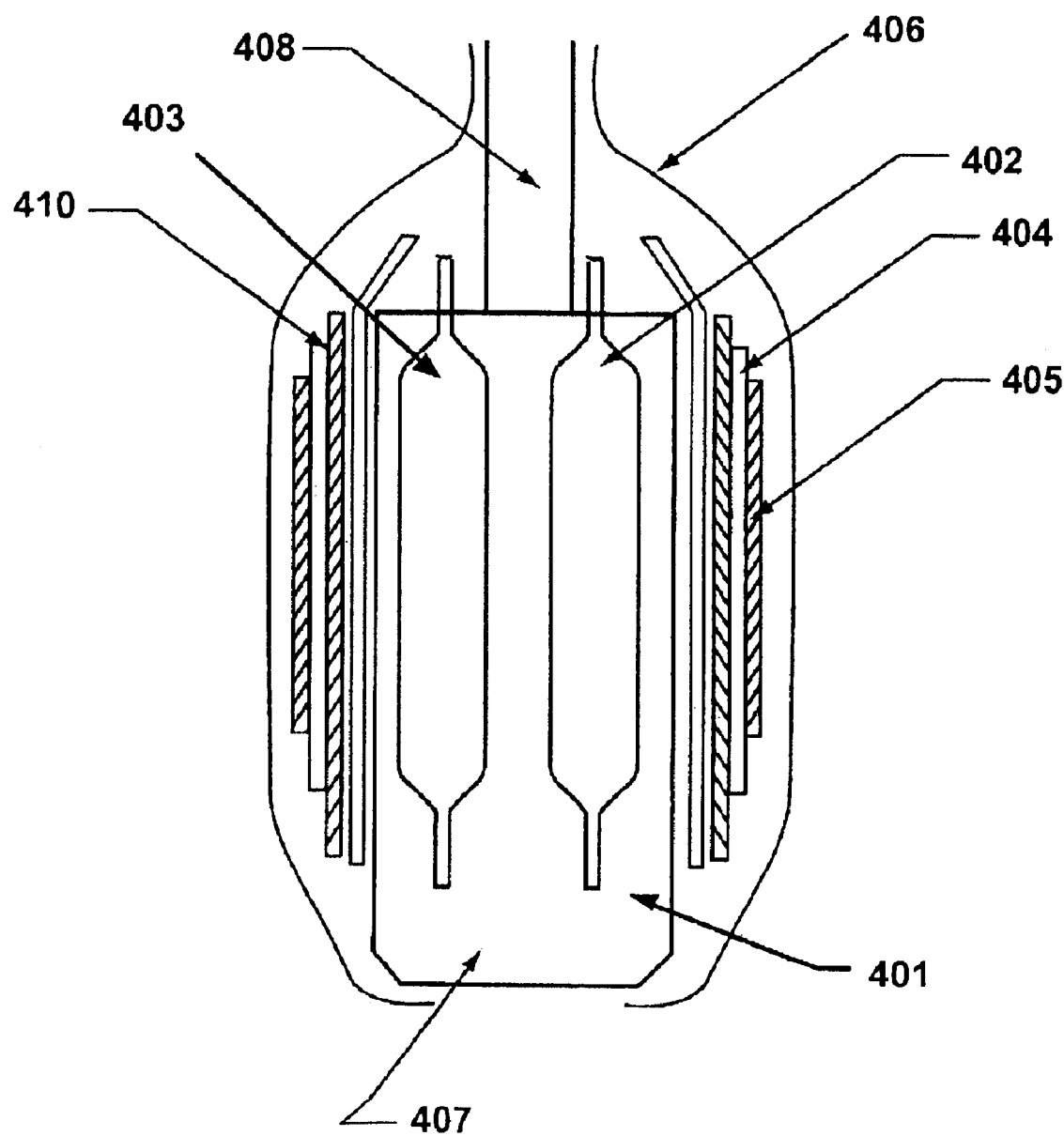
FIG. 7 is an illustration of a conformable probe having several balloon elements spanning the circumference of the probe.
Figure 8:
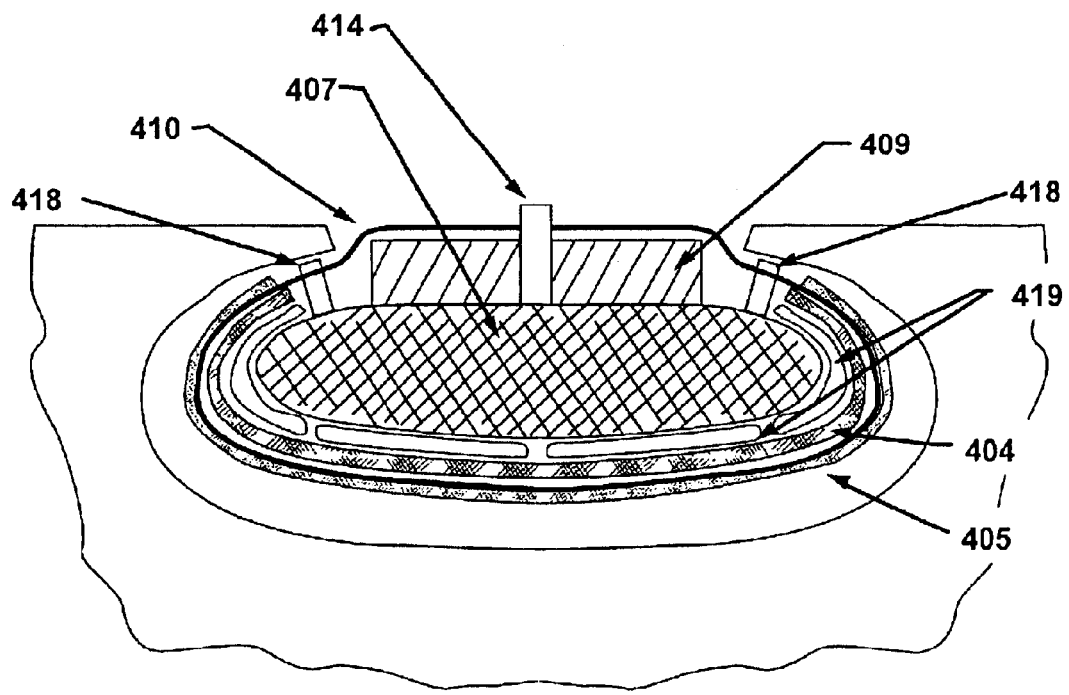
FIG. 8 is a cross-sectional view of the probe of FIG. 7.
Figure 9:
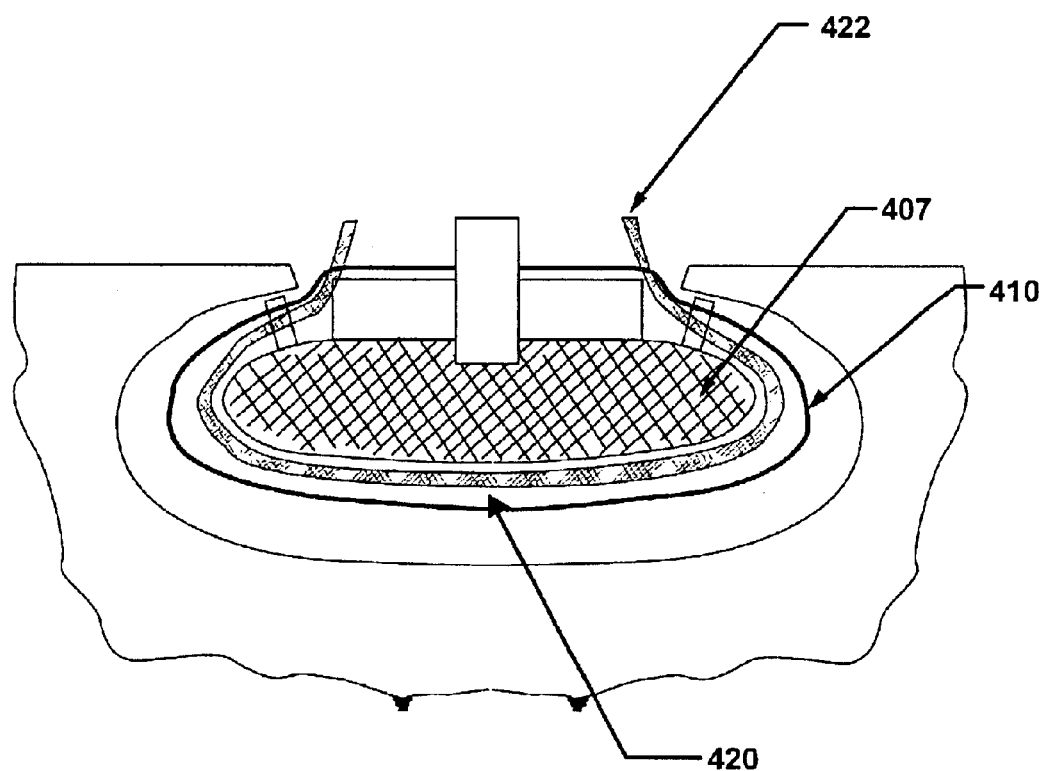
FIG. 9 is another cross-sectional view of the probe of FIG. 7.

The shuttle design of FIG. 7, FIG. 8, and FIG. 9 includes the use of multiple expandable chambers for providing uniform pressure along the inner surface of the MUT. The probe includes a body 401, expandable elements like plastic balloons 402 and 403, a soft foam layer 404, strips of low coefficient of friction plastic such as Teflon 406, a foam spring 409, a flexible but inelastic ring 410 and a sensor 405. The body includes an insert 407 that approximates the shape of the MUT and contains a handle 408. The insert 407 also includes four convex tabs 418 that prevent contact between the insert surface and the MUT surface. The space between the insert 407 and the MUT surface is filled with the sensor 405, the flexible inelastic ring 410, a foam layer 404, and balloons. A single balloon 420 can be used along or across (FIG. 9) the entire surface of the MUT or several balloons 419 can be used along the periphery (FIG. 8). The foam layer 404 helps to provide a more uniform pressure behind the sensor, particularly in regions near the edges of multiple balloons. The foam layer 404 may be unnecessary if the balloons provide sufficient conformability for the sensor against the test material surface. In addition, a foam spring 409 is located on the back portion of the insert surface between the openings of the MUT. The foam spring provides a force to the ring 410 that then presses on the balloons to flatten them when they are deflated. The foam layer 404 is a compressible element that assists the sensor in conforming to the surface of the MUT. The sensor is attached to the outer surface of the ring 410 for inspecting the MUT. The ring 410 is also attached to the strip 406 that connects the upper 412 and lower 413 portions of the body. The pin 414 maintains the spatial position of the ring 410 during the inflation and deflation of the balloons. Sleeves 422 are provided to connect to the balloons to a source of pressure.

Figure 10:
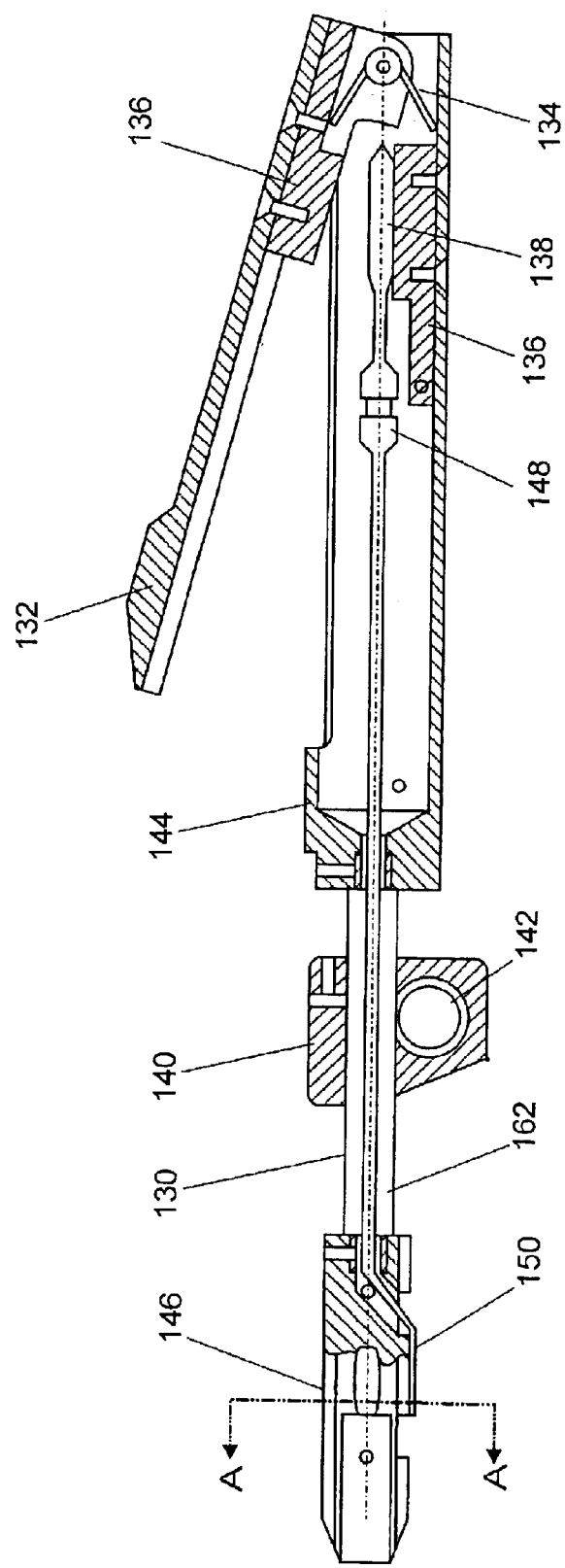
FIG. 10 is an illustration of a self-contained probe including both a shuttle and pressure source.
Figure 11:
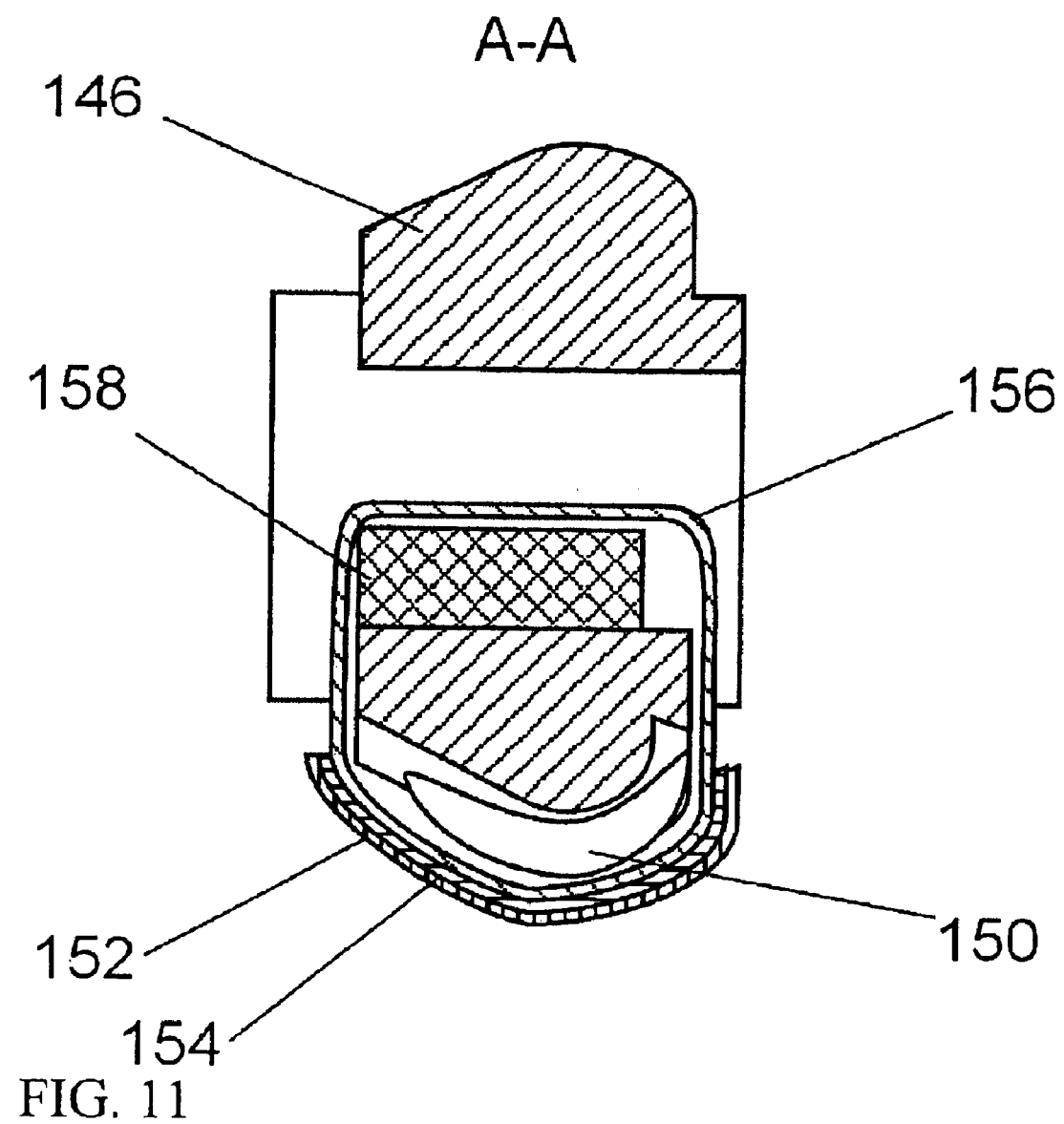
FIG. 11 is a cross-sectional view of the probe of FIG. 10 along the line A—A.

An embodiment of a probe for inspection of engine disk slots or other curved surfaces is illustrated in FIG. 10 and FIG. 11. This probe includes a shuttle 146, a body 144, and a connection tube 130. The shuttle 146 holds a balloon 150 and a sensor or sensor array, and provides smooth motion of the sensor or sensor array across the surface of the test material during the inspection. The body 144 contains means for applying pressure to the balloon 150 in the shuttle. The connection tube 130, keeps the assembly together, provides a support for the position encoder 140, and provides a hydraulic connection 162 to the shuttle balloon. Expansion of the balloon 150 presses the sensor 154 against the material surface. The body 144 includes a second balloon 138 and adapters and connectors 148 that connect and seal to the open ends of both balloons 138 and 150. The body also contains a handle 132, which can create pressure in balloon 138 as it is sandwiched between a pair of balloon supports 136. A torsion spring 134 provides a force for returning the handle to the initial open position when the handle is released. The position encoder incorporates an encoder roller 142 that rotates as the axial position of the probe tube 130 changes with insertion into the test article. The encoder roller 142 is surrounded by flexible silicon tubing to ensure that there is sufficient friction for the encoder roller to rotate as the probe tube position changes.

An expanded view of the shuttle is illustrated in FIG. 11. A flexible eddy current sensor or sensor array 154 is attached to a flexible ring 156 that surrounds the balloon 150, part of the solid portion of the shuttle 146, and a foam spring 158. The balloon 150 presses the sensor 154 against the test material with a uniform force during the inspection. The flexible ring 156 transmits the motion from the foam spring 158 to the sensor 154, which allows the foam spring to return the sensor 154 to its initial position and deflate the balloon 150 upon completion of an inspection. An outer protective layer 152 is also used to protect the sensor 154 and balloon 150 from wear and shearing forces. Preferably, the flexible material for the sensor, the surrounding ring, and the outer protective wear material is Kapton™.

In operation, the shuttle is slid into the test article with the balloon 150 deflated. Once inside the test article, the handle 132 is closed which compresses balloon 138 and inflates balloon 150. This, in turn, presses the sensor 154 against the surface of the test material for the inspection. After completion of the inspection, releasing the handle 132 causes the handle to move to the open position and the foam spring 158 inside the shuttle 146 deflates the balloon 150 back to its original form. Any fluid (gas or liquid) can be used to inflate and deflate the balloons. Typically, air or water is used.

Figure 12:
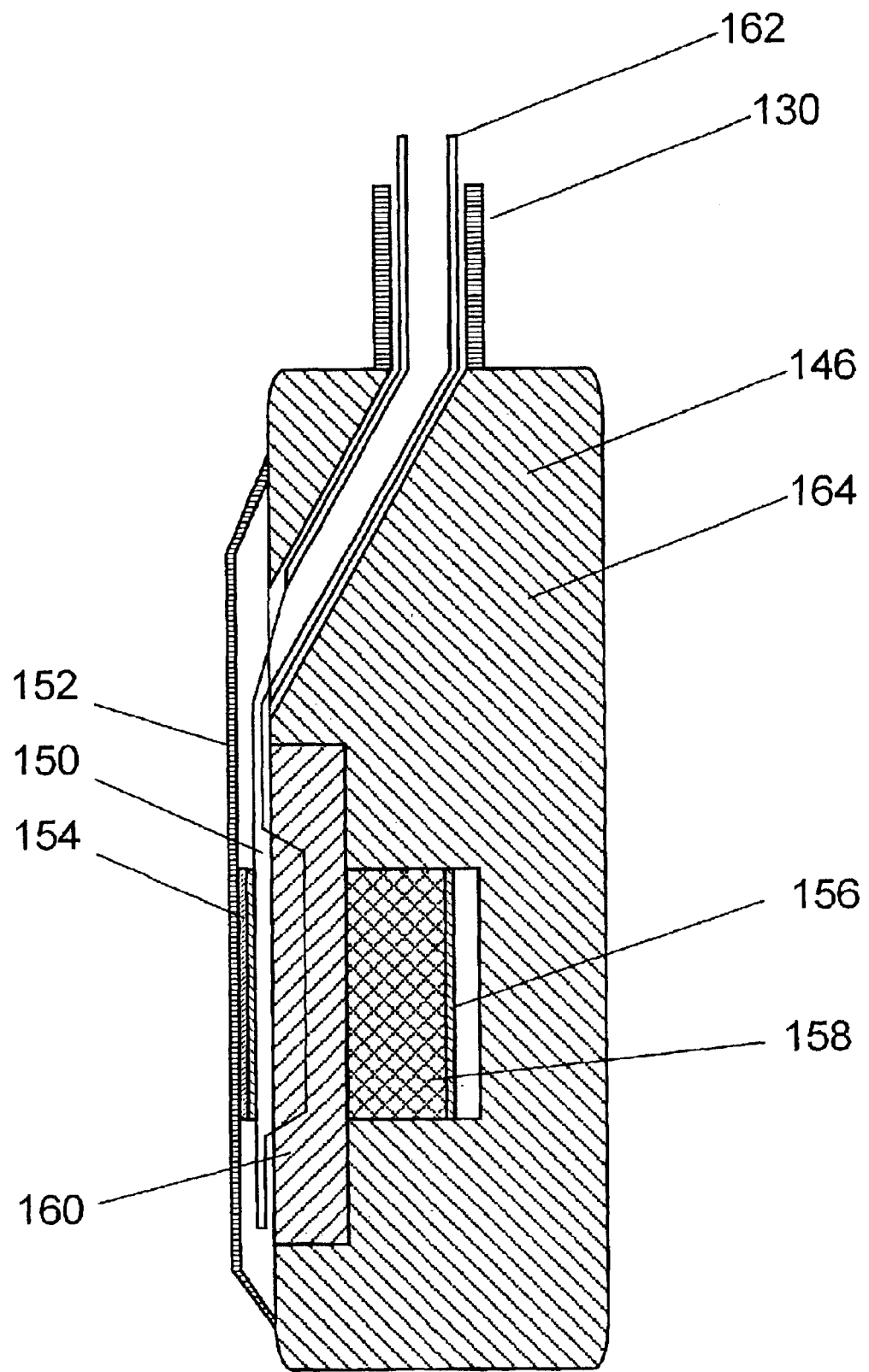
FIG. 12 is a cross-sectional view of a probe having a removable insert for ease of repair.
Figure 13:
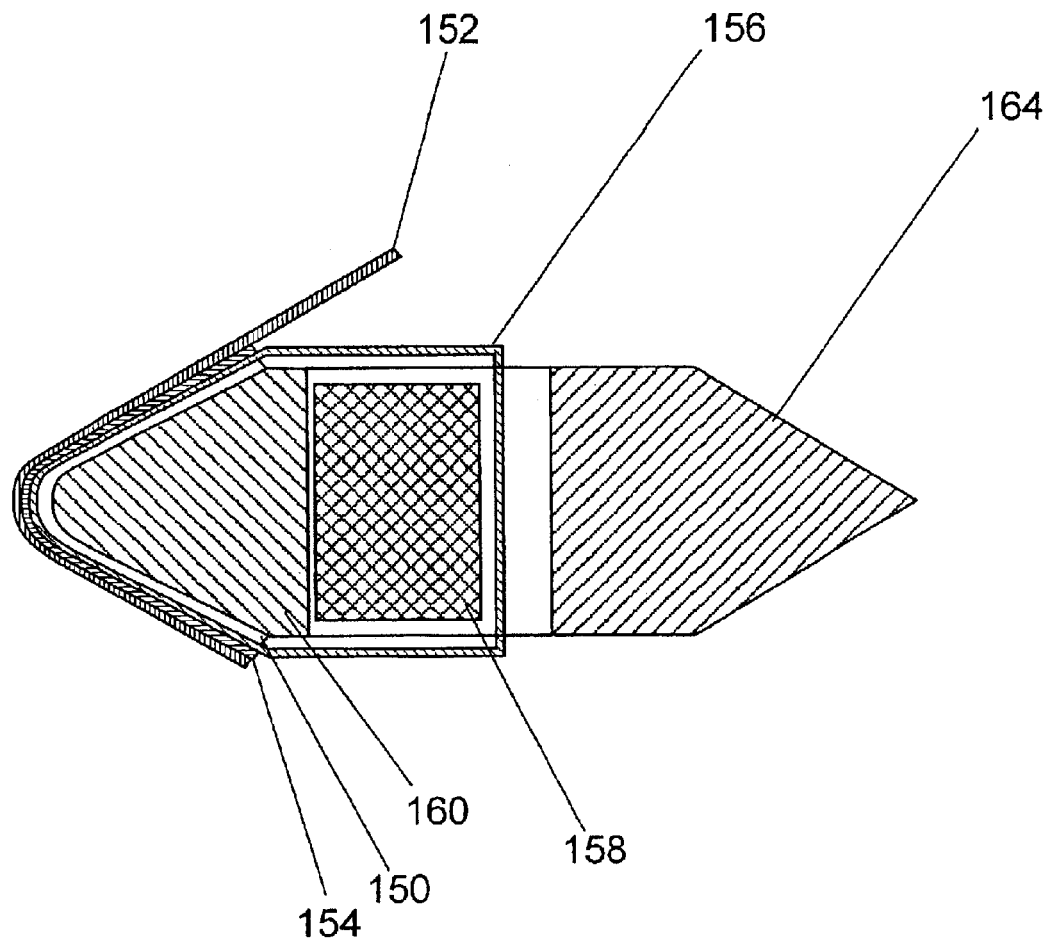
FIG. 13 is an expanded view of the probe of FIG. 12.

FIG. 12 and FIG. 13 show an alternative embodiment for the structure of the shuttle portion of the probe. In these embodiments, the shuttle 146 is split into two parts, a body 164 and a removable insert 160, with the removable insert attached to the body by means of a temporary adhesive. This modular design has the advantage that it allows rapid replacement of broken components. Removing the protection flexible layer 152 and the removable insert 160, provides easy access to the internal components of the shuttle.

Figure 14:
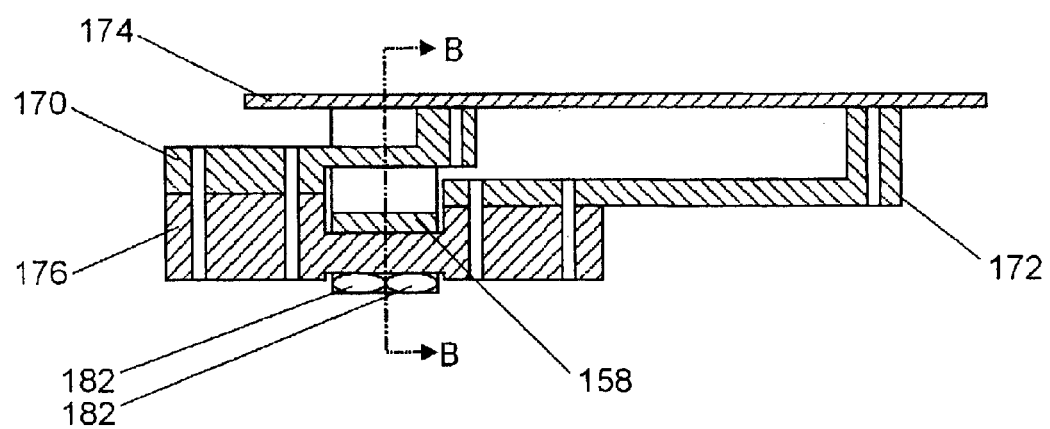
FIG. 14 is a cross-sectional view of a probe for a flexible eddy current sensor array.
Figure 15:
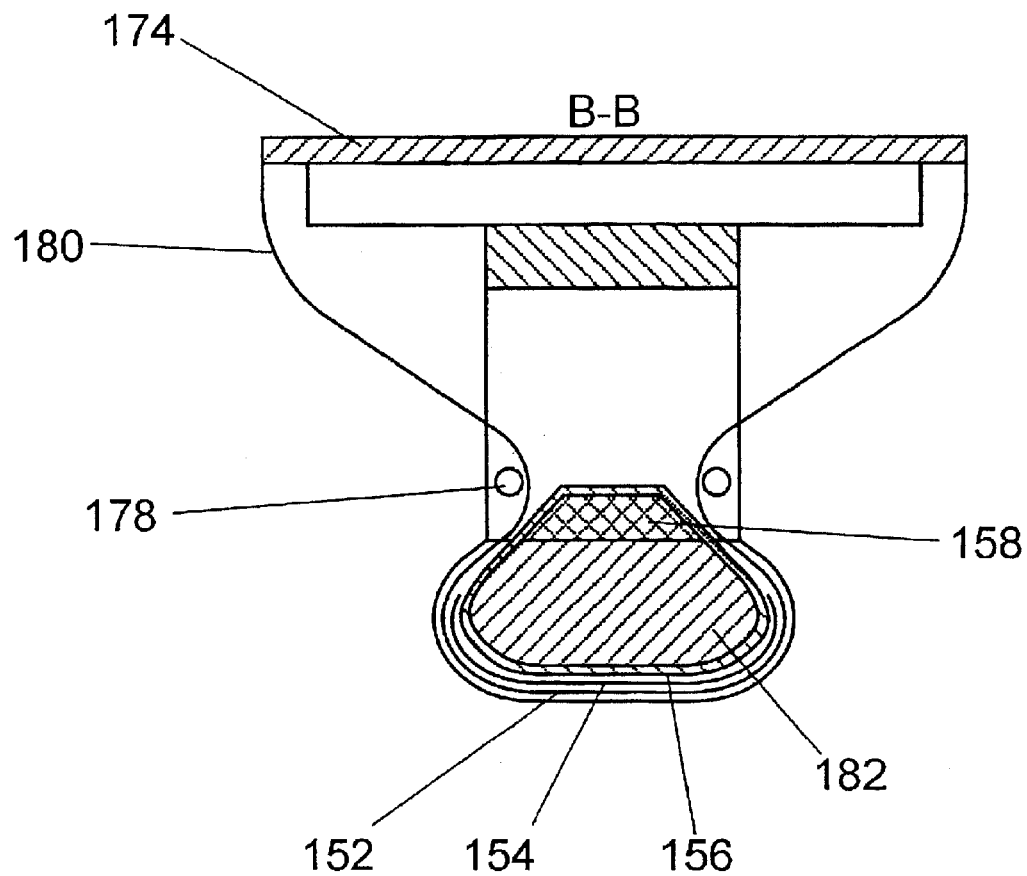
FIG. 15 is an expanded view of the probe of FIG. 14.
Figure 16:
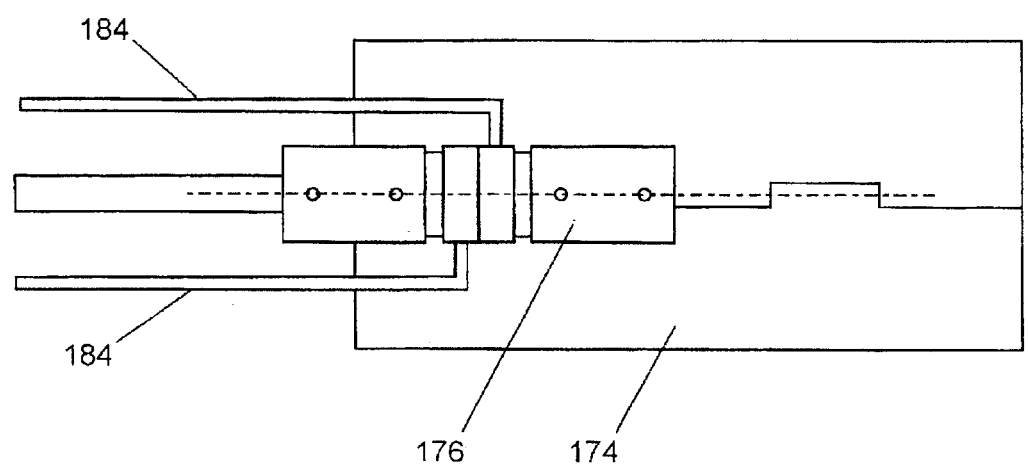
FIG. 16 is a bottom view of the probe of FIG. 14.

FIGS. 14–16 show an embodiment for a shuttle designed to accommodate a flexible eddy current sensor array having numerous leads for electrical connections to each of the sensing elements. The relatively large back plate 174 for the sensor provides a support structure for the bond pad connections to the sensing element leads. Support brackets 170 and 172 connect the back plate 174 to a mandrel 176. The mandrel carries balloons 182, a sensor array 154, foam spring 158, a flexible ring 156, and a protective flexible layer 152. The utility of each of these components is the same as was described for FIG. 11. The embodiment of FIG. 15 also includes a ring 178 that holds together flexible support structure 180 for the connection leads to the sensor array. Two or more balloons 182 are also oriented across the mandrel 176 for pressing the sensor against the material surface, such as an engine disk slot. The use of multiple balloons helps to force the sensor to conform to the surface of the test material even at edges, where the sensor may be entering or leaving the test article. This permits inspections close to the edges of engine disk slots and allows the sensor to conform to the surface geometry such as the chamfers at the ends of the slots. The sleeves 184 provide connections between the balloons 182 and the source of pressure.

Figure 17:
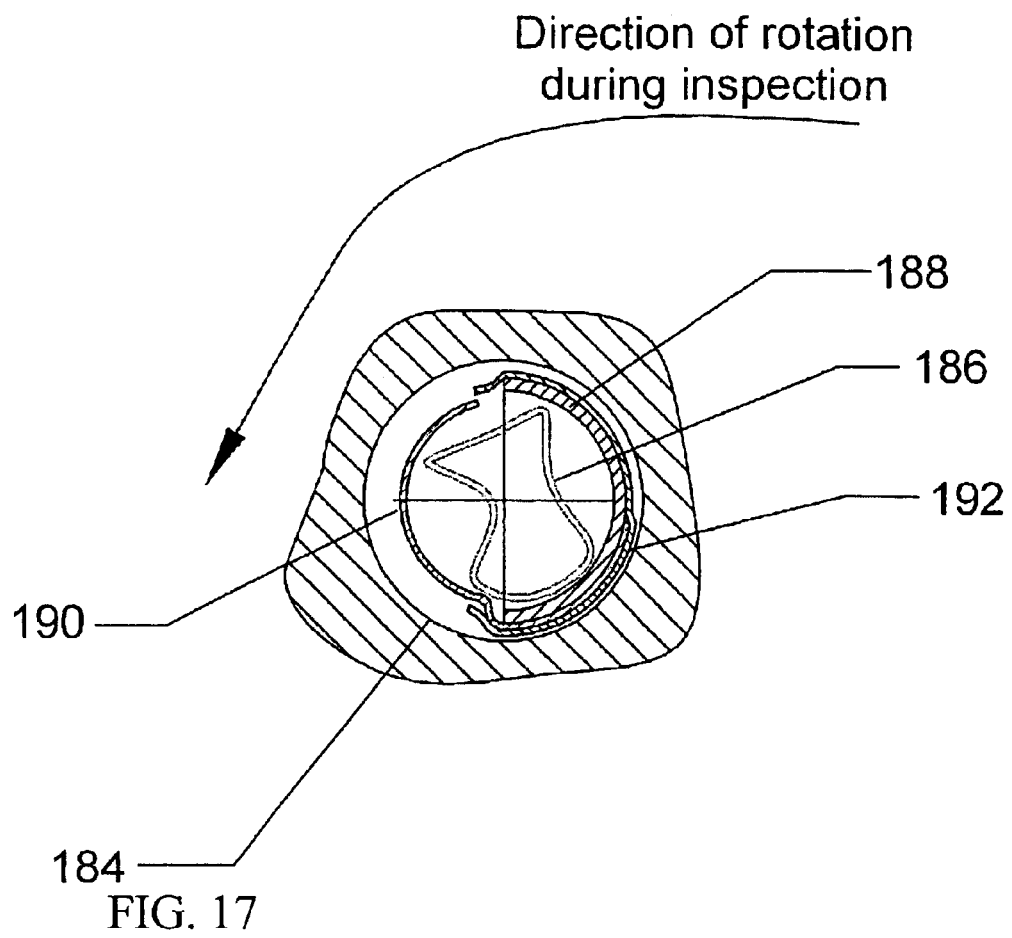
FIG. 17 is a cross-sectional view of a probe in a circular hole.
Figure 18:
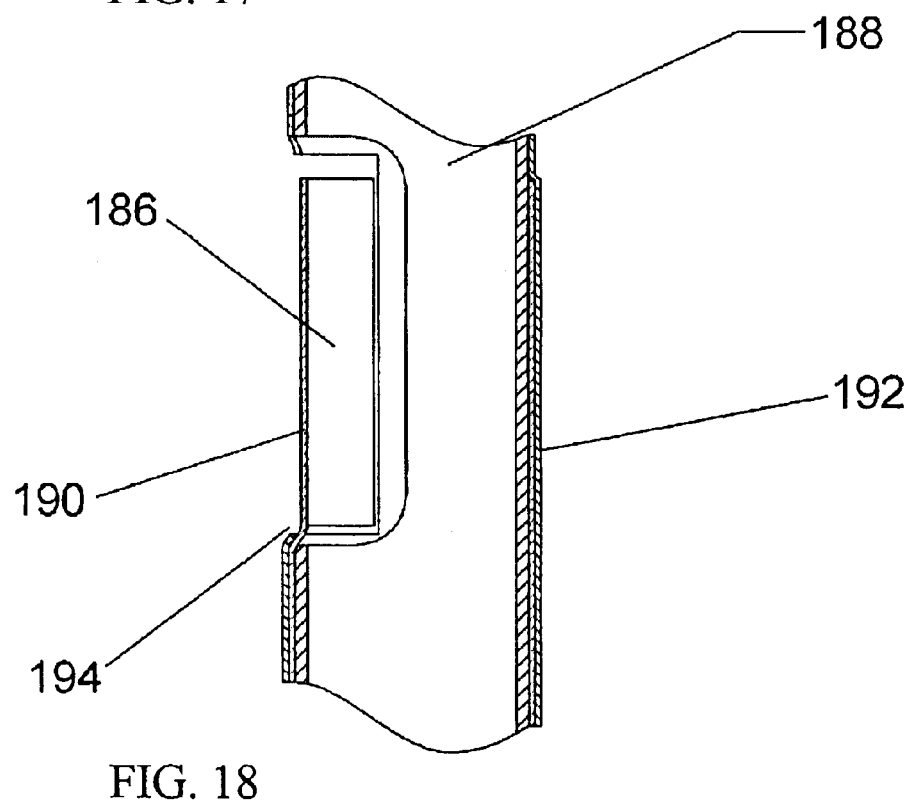
FIG. 18 is a side view of the probe of FIG. 17.

Probes incorporating an expandable balloon can also be designed for the inspection of circular holes. FIGS. 17 and 18 show a probe for inspection a circular opening in a material surface 184. A balloon 186 is placed inside the body 188 of a circular pipe. A sensor 190 is placed in an opening 194 cut out of the side of the body 188 for inspection of the material surface. The sensor 190 is held in placed and protected by material 192, which is preferably heat shrinkable tubing. The sensor 190 has its own spring or restoring force which allows it to maintain its shape and have a gradual curvature around the opening 194. During an inspection, the probe is inserted into the circular hole with the balloon deflated. The balloon is then inflated so that the sensor moves against the hole wall. The hole is then inspected by rotating the sensor around the hole and translating the sensor along the axis of the hole, which ensures complete coverage if the interior surface of the hole. An additional protective layer may be placed on the outside surface of the sensor 190, between the sensor and the test material surface 184, to protect the sensor and the probe.

Figure 19:
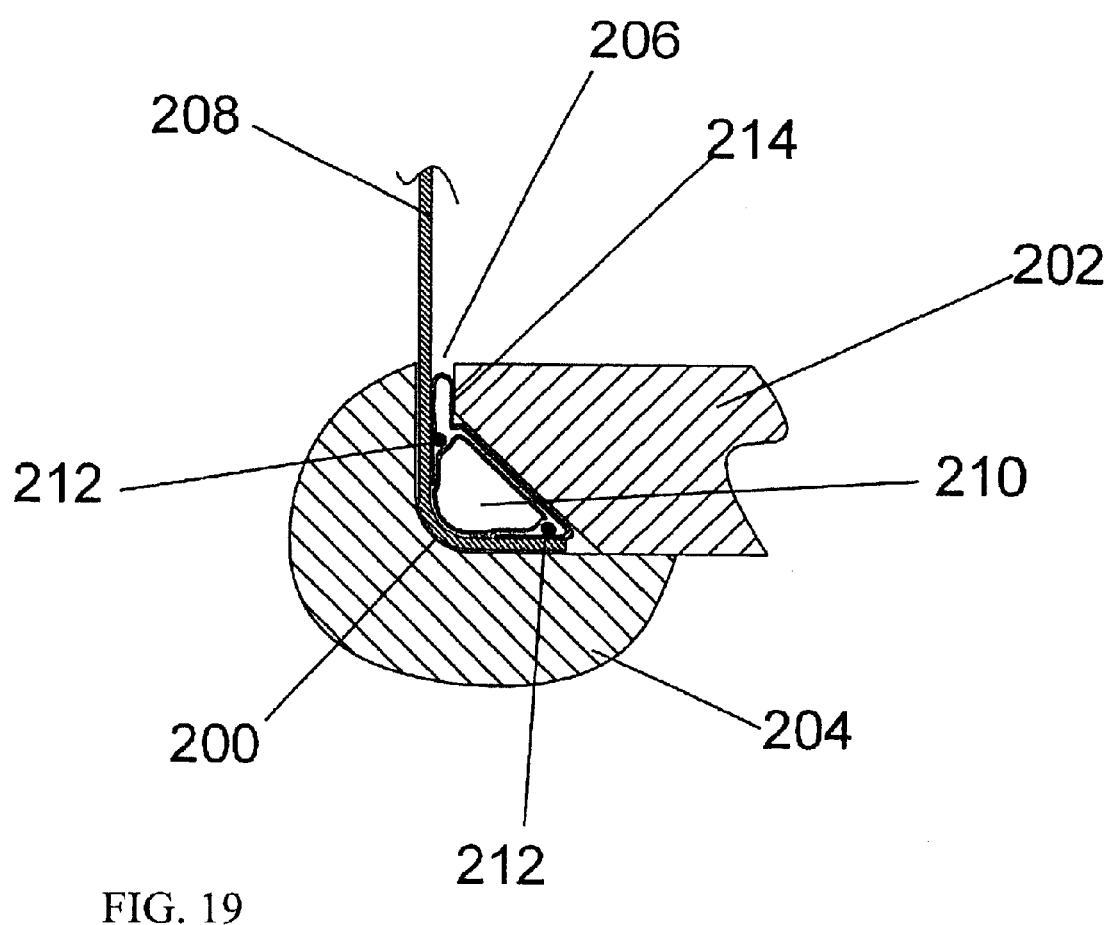
FIG. 19 is a cross-sectional view of a probe inside a region of limited access for inspection of the fillet.

The use of expandable balloons as an inherent part of a probe also permits material inspection in areas of limited access. FIG. 19 shows a cross-sectional view of a structural pylon beam on an aircraft where there is a need to inspect the fillet region 200 for flaws. The fillet 200 is on a body 204, which also has curvature out of the plane of the paper, and substantially covered by a bushing 202 so that access to the fillet is limited to a small opening 206. A flexible sensor 208 is placed between a balloon 210 and the fillet 200. Inflation of the balloon 210 moves the sensor against the fillet surface 200 and a deflated balloon 210 allows the sensor 208 to be inserted or withdrawn through the opening 206. Cables 212 are attached to the sides of the balloon 210 so that the balloon 210 and sensor 208 can be pulled along the fillet in either direction. A low friction film 214 is placed around the balloon 210 and cables 212 to protect the probe materials and to ensure smooth motion as the probe is moved past the test material surfaces. An additional protective layer may be placed between the sensor 208 and the test material fillet 200.

Figure 20:
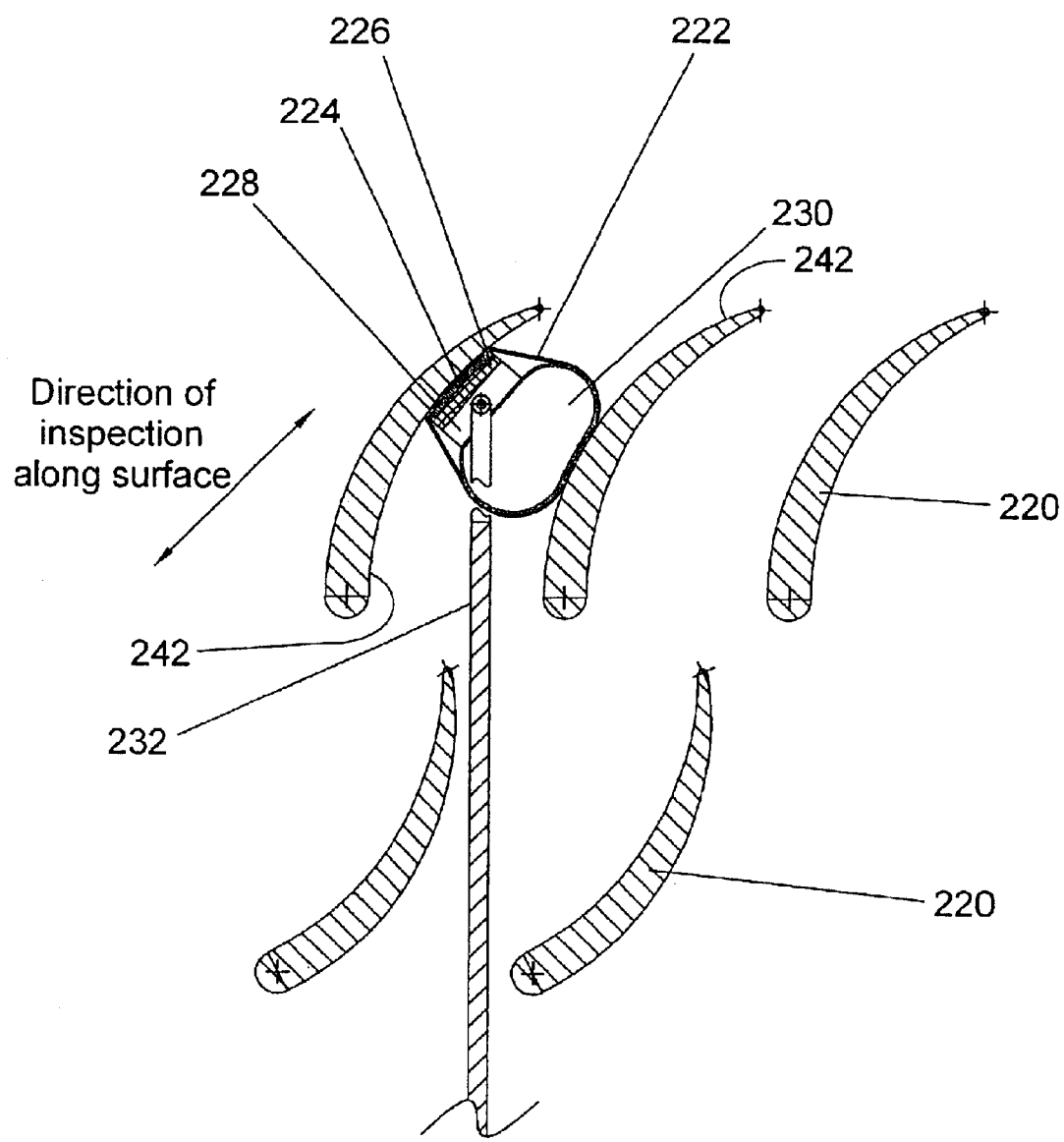
FIG. 20 is a cross-sectional view of a probe located between several turbine blades for inspection of the blade surfaces.

FIG. 20 shows another example of an inspection in a region of limited access, where there is a need to inspect the curved surfaces 242 of turbine blades 220 without removing all of the blades. This requires the capability to insert a probe between turbine blades 220 and being able to move the probe so that the surface of the blades can be inspected. In this case, a flexible but non-expandable ring 222 encircles the sensor 224, a foam layer 226, a rigid probe support 228 and a balloon 230. When deflated, the probe can be passed between the turbine blades 220. When inflated, the balloon expands to press against the surface 242 of a nearby blade, which also presses the sensor 224 against the surface 242 of the test material. The foam layer 226 ensures that the sensor conforms against the surface 242. Alternatively, a second balloon could also be used in place of the foam layer. A link mechanism 232 allows the probe to be inserted between the blades 220 and allows the operator to translate the sensor across the test material surface.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A device for inspecting a component comprising:
a flexible sensor that is placed against a component surface:
at least one elastic support member that locates the sensor proximate to the component surface;
at least one chamber in the at least one elastic support member, the flexible sensor being pressed against the component surface when the chamber is pressurized; and
a plurality of rigid cylinders positioned between the at least one elastic support and the sensor.

2. The device as claimed in claim 1 wherein the sensor is an eddy current sensor.

3. The device as claimed in claim 2 wherein the sensor is an eddy current sensor array.

4. A device for inspecting a component comprising:
a flexible sensor that is placed against a component surface;
at least one elastic support member that locates the sensor proximate to the component surface;
at least one chamber in the at least one elastic support member, the flexible sensor being pressed against the component surface when the chamber is pressurized; and
a plurality of support members positioned between the at least one elastic support and the sensor, the plurality of support members being elastic and conforming to the shape of the component surface when the chamber is pressurized.

5. A device for inspecting a component comprising:
a flexible sensor that is placed against a component surface;
at least one elastic support member that locates the sensor proximate to the component surface; and
at least one chamber in the at least one elastic support member, the flexible sensor being pressed against the component surface when the chamber is pressurized; and
at least one cylindrical core surrounded by a plurality of elastic support members which positions the at least one elastic support member near the component.

6. A device for inspecting a component comprising:
a flexible sensor that is placed against a component surface;
at least one elastic support member that locates the sensor proximate to the component surface; and
at least one chamber in the at least one elastic support member, the flexible sensor being pressed against the component surface when the chamber is pressurized; and
a compressible support layer placed between the sensor and the support members.

7. The device as claimed in claim 6 wherein the sensor is an eddy current sensor.

8. The device as claimed in claim 7 wherein the sensor is an eddy current sensor array.

9. A device for inspecting a component comprising:
at least one flexible sensor that is placed against a component surface;

at least one rigid support member for maintaining the sensor position proximate to the component surface; and at least one elastic member compartment a chamber, the flexible sensor being pressed against the component surface when the chamber is pressurized, the at least one elastic member being placed behind the sensor, between the sensor and the at least one rigid support member.

10. The device as claimed in claim 9 wherein the at least one rigid support member approximates the shape of the component surface.

11. The device as claimed in claim 10 further comprising a compressible support layer placed between the sensor and the at least one rigid support member.

12. The device as claimed in claim 9 further comprising a spring on the side of the at least one rigid support member opposite the at least one elastic member, and a flexible ring encircling the elastic member, rigid support, and spring.

13. The device as claimed in claim 12 wherein the at least one rigid support member is removable.

14. A device for inspecting a component comprising:
at least one flexible sensor that is placed against a component surface;
at least one elastic member containing a chamber, the flexible sensor being pressed against the component surface when the chamber is pressurized; and
at least one rigid support member for maintaining the sensor position proximate to the component surface, the rigid support member including a body and an actuated portion on the side of the body opposite the sensor that translates when the at least one elastic member is pressurized, and is held in place with a spring.

15. The device as claimed in claim 14 wherein the at least one elastic member is placed behind the body and the actuated portion.

16. The device as claimed in claim 15 wherein the shape of the component surface is concave, and the actuated portion presses against component surface.

17. The device as claimed in claim 16 wherein the actuated portion has a roller to ease relative motion between the inspection device and the component.

18. A device for inspecting a component comprising:
at least one flexible sensor that is placed against a component surface;
at least one elastic member containing a chamber, the flexible sensor being pressed against the component surface when the chamber is pressurized; and
at least one rigid support member for maintaining the sensor position proximate to the component surface, the at least one rigid support member forming a central core that is surrounded by a plurality of elastic members.

19. The device as claimed in claim 18 wherein the at least one rigid support member is placed between the pressurized chamber and the sensor.

20. A device for inspecting a component comprising:
at least one flexible sensor that is placed against a component surface;

a rigid support member that approximates the shape of the component surface;
at least one first elastic member containing a chamber capable of being pressurized and placed between the sensor and rigid support member, the flexible sensor being pressed against the component surface when the chamber is pressured.

21. The device as claimed in claim 20 wherein the component is an engine disk slot.

22. The device as claimed in claim 21 wherein the inspection involves measurement of surface roughness or damage.

23. The device as claimed in claim 22 wherein the surface damage is frening.

24. The device as claimed in claim 20 wherein the sensor is an eddy current sensor.

25. The device as claimed in claim 24, wherein the sensor is an eddy current sensor array.

26. The device as claimed in claim 20 further comprising a spring on the side of the rigid support member opposite the at least one first elastic member and a flexible ring encircling the elastic member, rigid support, and spring.

27. The device as claimed in claim 26 wherein the rigid support member is removable.

28. The device as claimed in claim 20 further comprising at least one second elastic member containing a chamber that is configured to be pressurized, and is mechanically connected to and sealed to the at least one first elastic member, wherein compression of the second elastic member supplies pressure to the first elastic member.

29. A device is for inspecting a component comprising:
a flexible sensor that is placed against a component surface;
an elastic member positioned behind the sensor containing a chamber capable of being pressurized the flexible sensor being pressed against the component surface when the chamber is pressurized;
at least one cable placed on a side of the elastic member and held in place by a flexible film for adjusting the sensor position; and
means for supplying pressure to the chamber off the elastic member.

30. A device is for inspecting a component comprising:
a flexible sensor that is placed against a component surface;
a rigid support member for adjusting the sensor position;
an elastic member containing a chamber capable of being pressurized the flexible sensor being pressed against the component surface when the chamber is pressurized; and
a second rigid support positioned between the sensor and the elastic member and a flexible ring encircling the elastic member, the second rigid support, and sensor.

31. The device as claimed in claim 30 further comprising a compressible support layer placed between the second rigid support and the sensor.

* * * * *

UNITED STATES PATENT AND TRADEMARK OFFICE
CERTIFICATE OF CORRECTION

PATENT NO. : 6,798,198 B2
DATED : September 28, 2004
INVENTOR(S) : Vladimir Tsukernik et al.

It is certified that error appears in the above-identified patent and that said Letters Patent is hereby corrected as shown below:

<u>Column 10,</u>
Line 10, delete ":" and insert -- ; --;
Line 41, delete "and".

<u>Column 11,</u>
Line 4, delete "compartment" and insert -- containing --;
Line 41, insert -- the -- between "against" and "component".

<u>Column 12,</u>
Line 7, delete "pressured" and insert -- pressurized --;
Line 15, delete "frening" and insert -- fretting --;
Line 37, insert -- , -- after "pressurized"; and
Line 44, delete "off" and insert -- of --;
Line 52, insert -- , --after "pressurized".

Signed and Sealed this

Twenty-second Day of February, 2005

JON W. DUDAS
*Director of the United States Patent and Trademark Office*